United States Patent [19]

Zysman et al.

[11] Patent Number: 5,431,905
[45] Date of Patent: Jul. 11, 1995

[54] TRIGLYCEROL ALKYLCARBAMATES, THEIR PREPARATION AND THEIR USE AS EMULSIFYING AGENTS IN COSMETIC COMPOSITIONS IN THE FORM OF WAX MICRODISPERSIONS

[75] Inventors: Alexandre Zysman; Henri Sebag, both of Paris, France

[73] Assignee: L'Oreal, Paris, France

[21] Appl. No.: 281,974

[22] Filed: Jul. 29, 1994

Related U.S. Application Data

[60] Division of Ser. No. 974,171, Nov. 10, 1992, Pat. No. 5,371,252, which is a continuation of Ser. No. 589,651, Sep. 28, 1990, abandoned.

[30] Foreign Application Priority Data

Sep. 29, 1989 [FR] France ............................. 89 12750

[51] Int. Cl.$^6$ ..................... A61K 7/06; A61K 7/075; A61K 7/11
[52] U.S. Cl. ................. 424/70.8; 424/70.11; 424/70.19; 424/70.21; 424/70.31
[58] Field of Search ................ 424/70.8, 70.11, 70.19, 424/70.21, 70.31

[56] References Cited

U.S. PATENT DOCUMENTS 4,425,329 1/1984 Tsutsumi et al ...................... 424/70
5,306,488 4/1994 Vanlerberghe et al. .............. 424/71

FOREIGN PATENT DOCUMENTS 1250808 6/1969 Germany .
1617073 2/1971 Germany .

OTHER PUBLICATIONS

Barton and Ollis "Comprehensive Organic Chemistry", vol. 2, Part 9, pp. 1083–1084. (1985).
Barton and Ollis "Comprehensive Organic Chemistry", vol. 2, Part 9, p. 1070. (1985).
Barton and Ollis "Comprehensive Organic Chemistry", vol. 1, Part 4, pp. 676–678. (1985).

*Primary Examiner*—José G. Dees
*Assistant Examiner*—Barbara S. Frazier
*Attorney, Agent, or Firm*—Cushman Darby & Cushman

[57] ABSTRACT

A compound of the formula:

$$R-NHCOOCH(CH_2OCH_2CHOHCH_2OH)_2 \qquad (I)$$

wherein R is a $C_{10}$–$C_{20}$ alkyl, optionally unsaturated, is employed in the preparation of wax microdispersions useful particularly in cosmetic composition for the hair.

8 Claims, No Drawings

TRIGLYCEROL ALKYLCARBAMATES, THEIR PREPARATION AND THEIR USE AS EMULSIFYING AGENTS IN COSMETIC COMPOSITIONS IN THE FORM OF WAX MICRODISPERSIONS

This is a division of application Ser. No. 07/974,171, filed Nov. 10, 1992, now U.S. Pat. No. 5,371,252, which is a Continuation of application Ser. No. 07/589,651, filed Sep. 28, 1990, now abandoned.

The present invention relates to new esters of polyols, to their preparation and to their use, principally, as surfactant agents.

French patent No. 84.11687 (2.549.826) describes monoethers of fatty alcohols and triglycerol, useful principally as emulsifying agents in cosmetic compositions, and their preparation, in the form of well defined compounds, from the bisisopropylidene derivative of linear triglycerol.

It has now been discovered that certain triglycerol alkylcarbamates exhibit interesting surfactant properties, which permit their use, principally, in the preparation of cosmetic compositions.

Moreover, it is known that it is possible to obtain indefinitely, with certain waxes, stable and water dilutable microspheres, without aggregation or sedimentation of the particles in suspension. The microdispersions of waxes are obtained by melting the wax in the presence of a surfactant and, depending on circumstances, a portion of water, then progressively adding hot water with stirring. The intermediate formation of a water-in-oil type emulsion is observed followed by a phase inversion with the final production of an oil-in-water type emulsion. On cooling, a stable microdispersion of solid colloidal wax particles is obtained; see for example, *"Microemulsions Theory and Practice"*, L. M. Prince Ed., Academic Press (1977), pages 21–32.

Research carried out by the applicants has shown that the monoethers of triglycerol disclosed in the above-mentioned French patent do not permit the production of a wax microdispersion.

On the other hand, it has been found that the triglycerol alkylcarbamates of the present invention do permit the production of wax microdispersions.

Such wax microdispersion are useful principally as supports for cosmetic composition for the hair. This use in the subject of Luxembourg patent application No. 87.457 filed on Feb. 24, 1989 and entitled: "Use as cosmetic composition for the hair, a wax microdispersion, and process for the treatment of hair with such a composition".

It has also been discovered that the triglycerol alkylcarbamates exhibit, relative to the ethers of the aforementioned French patent, improved cutaneous tolerance.

The present invention thus relates to alkylcarbamates having the following formula:

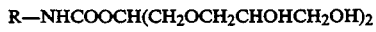  (I)

wherein
R represents alkyl, optionally unsaturated, having 10–20 carbon atoms.

In the compounds of formula I, the R group can represent principally n-decyl, n-dodecyl, n-tetradecyl, n-hexadecyl, n-octadecyl, n-octadecenyl (oleyl), 2-hexyldecyl, 2-octyldodecyl, 2-heptylundecyl, etc.

The present invention also relates to a process for preparing the compounds of formula I.

This process comprises reacting a compound of the formula:

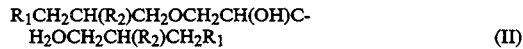  (II)

wherein $R_1$ and $R_2$, taken together, form a divalent group of the formula: $-O-CR_3(R_4)-O-$,
$R_3$ and $R_4$, each independently, represent lower alkyl, and
wherein
the hydroxyl group of the compound of formula II is active in the form of imidazolide or chloroformate, with an amine, $RNH_2$, wherein R is defined above, so as to obtain a compound having the formula:

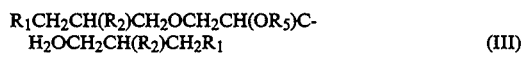  (III)

wherein $R_5$ represents $-CO-NHR_1$ and then hydrolyzing said compound III so as to obtain the corresponding compound having formula I.

Activated compound II has formula IIA:

  (IIA)

wherein $R_6$ represents

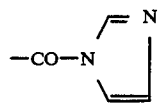

or $-CO-Cl$.

The IIA compound (imidazolide) can be obtained by reacting compound II (non-activated) with carbonyldiimidazole.

The reaction of carbonyldiimidazole and the compound of formula II is carried out by dissolving these reactants in a solvent such as tetrahydrofuran or dichloromethane. The resulting solution is stirred for a few hours at a temperature between 20° C. and the boiling temperature of the solvent. The resulting imidazolide of formula III can be used directly for subsequent reactions.

Starting with compound II, it is also possible to prepare, in accordance with known methods, the corresponding chloroformate, of formula IIA wherein $R_6$ is $-COCl$.

For reaction with the amine, the compound of formula IIA is dissolved in a solvent such as dichloromethane. The amine, $RNH_2$, is then added in the form of a solution, for example, in dichloromethane. In the case where compound IIA is a chloroformate, the reaction is carried out in the presence of an HCl acceptor, such as pyridine or triethylamine. The reaction medium is stirred at a temperature between, for example, 20° C. and the boiling temperature of the solvent, for several hours. The organic phase is then washed several times with water and dried, for example, on sodium sulfate. The solvent is removed by evaporation under reduced pressure. The resulting compound of formula III can be submitted directly to hydrolysis.

Hydrolysis is carried out, for example, in a solvent such as methanol, ethanol or tetrahydrofuran in the presence of a small amount of water and a protonated acid.

There can be employed mineral acids such as sulfuric acid, phosphoric acid or hydrochloric acid, or organic acids such as paratoluene sulfonic acid. Preferably hydrochloric acid is used.

The amount of acid can vary, for example, from 0.05 to 0.2 mole, and preferably from 0.05 to 0.1 mole, of acid relative to the number of moles of the compound of formula III.

The initial reactants employed in the process of the present invention are known or can be prepared in a known manner. The diisopropylidene triglycerol (formula II wherein $R_3=R_4=$methyl) is a commercial product sold by Solvay.

The present invention also relates to the use of the compounds of formula I as surfactants, and principally as emulsifying agents, in cosmetic compositions or in supports for cosmetic compositions. A particularly interesting use of the compounds of formula I is as dispersing agents in the preparation of aqueous wax microdispersions.

This use is principally characterized by the fact that the wax and at least one compound of formula I are heated to a temperature greater than the melting temperature of the wax, but not greater than 100° C., optionally in the presence of a part of water, until complete melting of the wax. Water, or the remainder of the water, is progressively added, the water being at a temperature at least equal to the said temperature at which the wax is being heated. The mixture is then stirred until a wax microdispersion in a continuous aqueous phase is formed. The resulting wax microdispersion is then cooled to ambient temperature.

The present invention also relates to wax microdispersions which can be obtained by the above described process.

Representative useful waxes include, principally, waxes or mixtures of waxes having a final melting point greater than 60° C. but lower than 100° C.

The emulsifying agent comprises at least one compound of formula I, optionally in admixture with other nonionic or anionic emulsifying agents.

The microdispersion can contain, for example, from 0.1 to 40 percent by weight of wax and from 0.01 to 25 percent by weight of emulsifying agent.

Preferably, the wax/emulsifying agent weight ratio varies from 1 to 30.

Generally, the wax microdispersion contains at least 35 percent of water.

In the resulting wax microdispersion, the size of the wax particles is lower than 500 nm.

Representative useful waxes include, for example, Carnauba wax, Candelilla wax, Alfa wax and mixtures thereof.

The cited waxes or mixture thereof can also be employed in combination with another wax or a mixture of other waxes, for example with a paraffin wax; the weight amount of Carnauba wax and/or Candelilla wax, in such mixtures, is preferably greater than or equal to 50%.

The surfactants which can be employed in admixture with the compounds of formula I are, for example, anionic surfactants having, for example, a lipophile-hydrophile balance (HLB) ranging form 10 to 40. They are, principally, salts of fatty acids (for example, alkaline salts or organic salts such as salts of amines), the said fatty acids having, for example, 12 to 18 carbon atoms and being able to have a double bond as in the case of oleic acid; the alkaline salts or salts of organic bases of alkyl-sulfuric and alkyl-sulfonic acids having 12–18 carbon atoms, of alkyl-arylsulfonic acids whose alkyl chain contains from 6 to 16 carbon atoms, the aryl moiety being, for example, a phenyl group. They are also ether-sulfates, in particular the products of sulfating fatty alcohols and polyalkoylated alkylphenols, in which the aliphatic chain has from 6 to 20 carbon atoms and the polyalkoxylated chain has from 1 to 30 oxyalkylene units, in particular oxyethylene, oxypropylene or oxybutylene units.

The nonionic surfactants which can be employed in admixture with the compounds of formula I are, principally, fatty acids or amides of polyalkoxylated and/or polyglycerolated fatty acids; esters of fatty acids and polyalkoxylated and/or polyglycerolated polyols fatty alcohols or polyalkoxylated and/or polyglycerolated alkylphenols alkanediols or 1,2- or 1,3-alkenediols, polyalkoxylated and/or polyglycerolated; and alkylethers of alkanediols or 1,2- or 1,3-alkenediols, polyalkoxylated and/or polyglycerolated. The fatty acids or alcohols, optionally unsaturated, have for example, 12 to 24 carbon atoms. The alkyl chain of the alkylphenols has, for example, 6 to 16 carbon atoms, the alkanediols or alkenediols have from 9 to 24 carbon atoms, the alkyl of the alkylethers has from 4 to 20 carbon atoms, and the number of oxyalkylene units or $(-CH_2-CHOH-CH_2O-)$ units can range from 2 to 40.

The polyalkoxylated nonionic derivatives are principally polyoxyethylenated derivatives, optionally polyoxypropylenated.

The polyalkoxylated fatty acids are commercial products, and principally products sold under the trade name "Myrj" by ICI Americas.

The esters of fatty acids and polyoxyethylenated polyols for which the polyol is sorbitol are know products sold under the trade name "TWEEN" by ICI Americas.

The polyoxyethylenated fatty alcohols are commercial products, and principally those sold under the trade name "Brij" by ICI Americas.

The polyglycerolated fatty alcohols or polyglycerolated alkanediols or alkenediols, or alkylethers of polyglycerolated alkanediols or alkenediols can be prepared, for example, in accordance with the procedures described in French patents 1.477.048, 2.025.681, 2.091.516 and 2.465.780 or in accordance with analogous methods.

The fatty acids or amides of polyglycerolated fatty acids are principally described in French patent 1.484.723 or are again commercial products such as those sold under the trade name "Plurol" by Gattefosse or "Drewpol" by the Stefan Company.

The present invention also relates to cosmetic compositions and principally cosmetic composition for the hair, characterized by the fact that they contain as a surfactant or emulsifying agent, at least one compounds of formula I.

The compositions of the present invention can contain, however, all conventional active adjuvants, vehicles and secondary components that are desired to be included in the compositions.

The cosmetic compositions of the present invention can be provided principally in the form of stable wax microdispersions which have been described above. These compositions in the form of wax microdispersions are useful principally as hair styling lotions and also lotions intended to improve the appearance of hair of persons having oily hair, as is described in the Luxembourg patent application cited above.

These compositions in the form of microdispersions can contain one or more conventional secondary adjuvants such as thickening agents, stabilizers, perfumes or preservatives.

These secondary adjuvants are added according to the situation either with the initial reactants (prior to preparing the microdispersion) or in the final composition.

The nonvolatile hydrosoluble adjuvants can be added optionally in the water employed to produce the microdispersion.

The liposoluble adjuvants are generally added to the wax before the production of the microdispersion.

These compositions can be applied to dry or wet hair, for example, before or after a shampoo. They can be rinsed or non-rinsed and can be applied daily.

When they are applied before or after a shampoo, the application being followed or not with a water rinse, they discipline or control the hair and impart hold and volume to the styling. In addition, they delay a hair re-oiling phenomenon which is observed with persons having oily hair.

These compositions have a pH which can vary from 3 to 10. The pH optionally can be adjusted using a conventional pH modifying agent.

The following non-limiting examples illustrate the present invention.

EXAMPLE 1

Compound of formula I wherein R=hexadecyl (a) Preparation of the imidazolide 102 g (0.63M) of carbonyldiimidazole are dissolved in 500 cm$^3$ dichloromethane. To this solution there are added 500 cm$^3$ of dichloromethane containing 200 g (0.62M) of diisopropylidene triglycerol, sold by Solvay. The reaction medium is stirred for 5 hours at ambient temperature and then washed four times with 150 cm$^3$ of water. The reaction medium is then dried on sodium sulfate and the solvent is evaporated under reduced pressure. 241 g of a compound in the form of an oil are obtained, the purity of which is sufficient for direct use in the following reactions.

(b) Reaction with hexadecylamine 14.1 g (0.034M) of the imidazolide prepared above are dissolved in 50 cm$^3$ of dichloromethane. To this solution 7.2 g (0.03M) of hexadecylamine dissolved in 25 cm$^3$ of dichloromethane are added. The reaction medium is then stirred overnight at ambient temperature. It is then washed several times with water. After drying the organic phase on sodium sulfate, followed by evaporation of the solvent under reduced pressure, 20 g of a waxy compound are recovered.

(c) Hydrolysis 20 g of the waxy compound obtained above are dissolved in 100 cm$^3$ of methanol to which 2 cm$^3$ of 5N HCl have been added. The reaction mixture is stirred overnight. After filtering some slight insolubles, the solvent is removed under reduced pressure. 17 g of a wax are obtained and recrystallized in a 200:30 mixture of heptane and ethyl acetate. 13 g of a white wax having a Kraft point at 0.5% of 21°–24° C. and a cloud point >100° C. are recovered. This product responds to formula I wherein R is hexadecyl.

The NMR $^1$H and $^{13}$C spectra are in accord with the structure indicated.

| | Elemental analysis | |
|---|---|---|
| | Calculated | Found |
| C% | 61.51 | 61.2 |
| H% | 10.52 | 10.23 |
| N% | 2.76 | 2.63 |

EXAMPLE 2

Compound of formula I wherein R is dodecyl

To 100 cm$^3$ of a solution of dichloromethane containing 54 g (0.13 mole) of the imidazolide of diisopropylidene triglycerol, prepared in accordance with Example 1(a), there are added 19.65 g (0.106 mole) of dodecylamine dissolved in 150 cm$^3$ of the same solvent. The reaction medium is stirred at ambient temperature overnight after which it is washed three times with 100 cm$^3$ of water. It is dried on sodium sulfate and the solvent is evaporated under reduced pressure. 62 g of a very lightly colored viscous oil are recovered.

60 g of this resulting oily product are dissolved in 300 cm$^3$ of methanol. 5 cm$^3$ of 5N HCl are then added. The reaction mixture is then stirred at ambient temperature overnight at which point the solvent is evaporated under reduced pressure. 49.2 g of a viscous oil are recovered.

30 g of this oil are purified on a silica column (Kieselgel 60, Merck) with, as eluant, a 90:10 mixture of dichloromethane and methanol.

12 g of a compound of formula I wherein R is dodecyl, in the form of a white wax, are recovered.

The NMR $^{13}$C spectrum is in accord with the structure indicated.

EXAMPLE 3

Compound of formula I wherein R is oleyl

To 100 cm$^3$ of a solution of dichloromethane containing 5 g (0.12M) of the imidazolide of diisopropylidene triglycerol, prepared in accordance with Example 1 (a), there are added 26.75 g (0.1M) of oleylamine dissolved in 100 cm$^3$ of the same solvent. The reaction mixture is then stirred for 5 hours and the solvent is then removed under reduced pressure. 76 g of an oil are recovered which is then purified by passage on a fritted glass filled with Kieselgel 60 H silica (Merck) and by eluting with a 9:1 mixture of dichloromethane and methanol.

After removal of the solvent under reduced pressure, 66 g of the compound in the form of an oil are recovered. 60 g of this oil are then hydrolyzed by dissolving it in 250 cm$^3$ of ethanol in the presence of 30 cm$^3$ of 1N HCl and by heating the reaction medium 4 hours at 60° C.

After removal of the solvent under reduced pressure the resulting wax is purified by passage on a fritted glass filled with Kieselgel 60 H silica and with, as eluant, a 95:5 mixture of dichloromethane and methanol.

40 g of the compound of formula I wherein R is oleyl are recovered in the form of a translucent wax.

The NMR $^{13}$C spectrum is in agreement with the structure indicated.

Examples of Preparing Wax Microdispersion—Examples A–D

These wax microdispersion are prepared in accordance with the method described above. The wax employed is Carnauba wax. The emulsifying agent is a compound of formula I. The constituents and the amounts thereof, as well as the physico-chemical characteristics of the resulting microdispersion (appearance, average diameter of the wax particles, polydispersivity) are set forth in the following Table:

| Example | Emulsifying agent R | Amount (%)[1] | Additive Nature | Amount (%)[1] | Amount of wax (%)[1] | Physico-chemical characteristics Appearance | Average diameter | Poly-dispersivity |
|---|---|---|---|---|---|---|---|---|
| A | $C_{16}H_{33}$ | 2.11 | KOH | 0.03 | 10 | yellowish opalescent liquid | 110 nm | 0.2 |
| B | $C_{12}H_{25}$ | 1.88 | DCP[2] | 0.09 | 10 | whitish liquid | 258 nm | 0.13 |
| C | " | " | KOH | 0.03 | 10 | whitish slight bloom liquid | 208 nm | 0.12 |
| D | $C_{18}H_{35}$ | 2.21 | KOH | 0.03 | 10 | yellowish opalescent liquid | 71 nm | 0.14 |

[1]weight percent relative to 100 g of dispersion in water
[2]DCP = Dicetylphosphate (sodium salt)

As a comparison an attempt was made to prepare a wax microdispersion under the same conditions (emulsifying agent: 1.93%; KOH: 0.03%; wax: 10%) using as the emulsifying agent a compound having the formula: $C_{16}H_{33}OCH(CH_2OCH_2CHOHCH_2OH)_2$. It was not possible to obtain a microdispersion.

Examples of Preparing Cosmetic Compositions (Examples CC1-CC5)

Example CC1

The following hair care composition is prepared by incorporation in the wax microdispersion the other adjuvants in the order indicated:

| | |
|---|---|
| Wax microdispersion, obtained in Example A | 98 g |
| Hydroxypropylmethylcellulose, sold by Dow Chemical under the trade name "METHOCEL F4M" | 1.5 g |
| Methylparahydroxybenzoate | 0.2 g |
| Derivative of imidazolidinyl urea, sold under the trade name "GERMALL 115" by Sutton Labs | 0.3 g |

This composition is applied to clean and dry hair, taking care to spread it all along the length of the hair. 2 to 5 g of the composition are used per head of hair. The resulting hair style exhibits fullness and is controlled or disciplined.

Example CC2

A before shampoo composition, in the form of a fluid gel, is prepared by incorporating in the wax microdispersion the other adjuvants, in the order indicated:

| | |
|---|---|
| Wax microdispersion obtained in Example B | 20 g |
| Crosslinked polyacrylic acid, (MW: 1,250,000), sold by Goodrich under the trade name "CARBOPOL 941" | 1 g |
| Derivative of imidazolidinyl urea, sold under the trade name "GERMALL 115" by Sutton Labs | 0.3 g |
| Sodium hydroxide, sufficient for pH = 7 | |
| Water, sufficient amount for | 100 g |

This composition is applied with good spreading to dry but not washed hair.

After a contact time of 2 to 3 minutes the hair is rinsed with water and then shampooed.

Soft, shiny and disciplined hair having volume or fullness is obtained.

Example CC3

A composition for the hair is prepared by incorporating in the wax microdispersion the other adjuvants, in the order indicated:

| | |
|---|---|
| 10% Carnauba wax microdispersion, prepared according to Example C | 99.65 g |
| Methylparahydroxybenzoate | 0.15 g |
| Derivative of imidazolidinyl urea, sold under the trade name "GERMALL 115" by Sutton Labs | 0.20 g |

This composition is used in the manner set forth in Example CC1.

The hair exhibits fullness after application of this composition and is disciplined and soft.

Example CC4

The following before-shampooing treating composition is prepared by incorporating in the wax microdispersion the other adjuvants in the order indicated:

| | |
|---|---|
| 10% Carnauba wax microdispersion, prepared in accordance with Example D | 97.5 g |
| Hydroxypropylcellulose, sold under the trade name "KLUCEL H" be Hercules | 2.0 g |
| Methylparahydroxybenzoate | 0.2 g |
| Derivative of imidazolidinyl urea, sold under the trade name "GERMALL 115" by Sutton Labs | 0.3 g |

The composition is applied under the conditions set forth in Example CC2. The hair thus treated exhibits much volume and is shiny and soft.

Example CC5

The following composition for the hair is prepared by incorporating in the wax microdispersion the other adjuvants, in the order indicated:

| | |
|---|---|
| Wax microdispersion obtained in Example C | 10 g |
| "CARBOPOL 941" | 1.5 g |
| NaOH | 0.6 g |
| PEG-15 COCAMINE | 3 g |
| GERMALL 115 | 0.2 g |
| Methylparahydroxybenzoate | 0.2 g |
| Potassium sorbate | 0.3 g |
| Perfume, sufficient amount | |
| Triethanolamine, sufficient amount for pH = 7 | |
| Water, sufficient mount for | 100 g |

PEG-15 COCAMINE: Polyethyleneglycolamine of copra acid, according to the definition of CTFA (Cosmetic, Toiletry and Fragrance Association), sold by Akzo under the trade name "ETHOMEEN C25".

This composition is applied with good spreading to dry and clean hair. After this treatment, the hair exhibits volume and is shiny and disciplined.

We claim:

1. In a cosmetic composition containing a surfactant or an emulsifying agent the improvement comprising as the surfactant or emulsifying agent, at least one compound of formula I $$R-NHCOOCH(CH_2OCH_2CHOHCH_2OH)_2 \quad (I)$$

wherein

R represents alkyl, optionally unsaturated, having 10 to 20 carbon atoms.

2. The cosmetic composition of claim 1 wherein R is selected from the group consisting of n-decyl, n-dodecyl, n-tetradecyl, n-hexadecyl, n-octadecenyl, n-hexyldecyl, 2-octyldodecyl and 2-heptylundecyl.

3. The cosmetic composition of claim 1 wherein said compound of formula I is provided in the form of a wax microdispersion in an aqueous liquid vehicle.

4. The cosmetic composition of claim 3 wherein said wax is selected from Carnauba wax, Candelilla wax, Alfa wax or mixtures thereof.

5. The cosmetic composition of claim 3 wherein the wax/emulsifying agent weight ratio ranges from 1 to 30.

6. The cosmetic composition of claim 3 wherein said emulsifying agent is present in an amount ranging from 0.01 to 25 weight percent.

7. The cosmetic composition of claim 3 wherein said wax is present in an amount ranging from 0.1 to 40 weight percent.

8. The cosmetic composition of claim 3 wherein the wax/emulsifying weight ratio ranges from 1 to 30.

* * * * *